United States Patent [19]

Okamoto et al.

[11] Patent Number: 5,981,594
[45] Date of Patent: Nov. 9, 1999

[54] METHOD OF TREATMENT FOR DIABETIC NEUROPATHY

[75] Inventors: Tasuku Okamoto, Tokyo; Masaharu Shiga, Kanagawa; Koji Miyata, Kanagawa; Yuji Kuwabara, Saitama; Shigeru Aoki, Tokyo; Hajimu Kurumatani, Kanagawa, all of Japan

[73] Assignee: Toray Industries, Inc., Japan

[21] Appl. No.: 09/037,400

[22] Filed: Mar. 10, 1998

[30] Foreign Application Priority Data

Mar. 11, 1997 [JP] Japan .................................. 9-056019

[51] Int. Cl.⁶ ..................... A61K 31/557; A61K 38/28; A61K 31/70; A61K 31/135
[52] U.S. Cl. ................... 514/573; 514/3; 514/35; 514/654; 514/866
[58] Field of Search ............... 514/573, 35, 654, 514/866, 3

[56] References Cited

U.S. PATENT DOCUMENTS 2,961,377 11/1960 Shapiro et al. ........................ 514/654
4,062,950 12/1977 Frommer et al. ...................... 514/35

FOREIGN PATENT DOCUMENTS 0248999 12/1987 European Pat. Off. .

OTHER PUBLICATIONS

Windholz et al., *The Merck Index*, 10th Ed. (1983) p. 723–724 ab.No. 4866

*Primary Examiner*—Kevin E. Weddington
*Attorney, Agent, or Firm*—Austin R. Miller

[57] ABSTRACT

A method of treatment for diabetic neuropathy using combined administration of a formulation including as an active ingredient a prostaglandin I derivative, especially a prostaglandin $I_2$ derivative with an anti-diabetic agent is applied to hypofunction of motor nerve and sensory nerve to which conventional anti-diabetic agents do not provide sufficient treatments, with nerve conduction velocities improved.

10 Claims, 1 Drawing Sheet

Changes in Nerve Conduction Velocity (median nerve)

Changes in Nerve Conduction Velocity (tibial nerve)

METHOD OF TREATMENT FOR DIABETIC NEUROPATHY

BACKGROUND OF THE INVENTION

1. Field of the Invention

The present invention relates to a method of treatment of diabetic neuropathy, which is a complication of diabetes.

2. Description of the Related Art

Diabetic neuropathy occupies an important place as one of three major complications of diabetes, along with retinopathy and nephropathy, because it develops at relatively earlier stages of diabetes among various other complications of diabetes. It occurs very frequently, ruins patients' quality of life, and leads to distinctively poor prognosis in cases where an autonomic disorder develops as a complication.

Diabetic neuropathy is currently categorized into three groups comprising mononeuropathy, symmetrical peripheral polyneuropathy and autonomic neuropathy (Williams Text Book of Endocrinology, 8th Edition, p. 1301, Harrison's Principles of Internal Medicine, 12th Edition, p. 1754).

Mononeuropathy is a focal or multifocal mononeural disorder which appears as lesions of the cerebral nerve or affects soma and/or extremities. Its major symptom emerges as dyskinesia in many cases. It is known to develop more often in elder patients.

Symmetrical peripheral polyneuropathy is the most frequent form of diabetic neuropathy. It generally makes slow progress, so that patients tend to become aware of the symptoms only after it has reached an advanced stage. The initial symptoms are often a reduced Achilles reflex and a decline or absence of vibratory sensibility. Urtication represented as a smarting feeling and then numbness on both feet follow.

With autonomic neuropathy, patients show representative symptoms for autonomic disorder, such as orthostatic hypotension, cardiac rate alteration, dyshidrosis, atony of esophagus or gastric atony, diabetic diarrhea, impotence and others.

As mechanisms for development of these symptoms, metabolic hypothesis and vascular/ischemic hypothesis have been implied. For the former hypothesis, hyperegasia of polyol metabolic pathway, a pathway where sorbitol and fructose are produced from glucose provided due to hyperglycemia is considered to be the major contributing factor. Another theory involving a reduced content of myoinositol is related to peripheral nerve disorder. In the latter hypothesis, neuro-microvascular occlusion and/or destruction of blood-nerve barrier are thought to be related to the nerve disorders.

For diagnosis and follow-up of diabetic neuropathy a variety of neurologic tests are required. In the first place, Achilles reflex, knee reflex, biceps reflex and triceps reflex are usually examined as deep reflexes. Other than that, tests are performed wherein thermal sensitivity is examined through unmyelinated fibers (C-fibers), cold sensation through small (thinly) myelinated fibers (A$\delta$-fibers), heat pain through A$\delta$-fibers and C-fibers, and cold pain through C-fibers. Accordingly, for testing sensory nerve functions, vibratory sensibility, pain sensation and thermal sensation (using both warm tests and cold tests) are examined (Clinical Medicine for Diabetic Neuropathy, edited by Masatada Hirata and Norihei Matsuoka, 1992, Gendai-Iryou-sha, p. 95).

Among various neurologic tests, nerve conduction velocity (NCV) examination is the most widely used as a method of objectively evaluating severity of diabetic neuropathy. For motor nerves, two different locations at a nerve are selected to be stimulated with intensities selected to induce the largest peak for each of the corresponding controlling muscles in electromyograms. Then the distance between the two locations is divided by the balance between the obtained latencies in the two electromyograms. The sensory nerve is electrically stimulated in the orthodromic direction at an intensity selected to obtain the largest action potential, and then the distance between the stimulated location and the induced location is divided by the latency.

As methods of treatment of diabetic neuropathy, it has been reported that some trial treatments have been conducted during the 1970s and 1980s based upon the hypothesis that abnormality of metabolic factors is viewed as a cause, Greene D A, De Jesus P V Jr., et al. (Effects of insulin and dietary myoinositol on impaired peripheral motor nerve conduction velocity in acute streptozatocin diabetes; J. Clin. Invest., 1975, 55, 6, 1326–36.) and Yagihashi S., Nishihira M., et al. (Morphometrical analysis of the peripheral nerve lesions in experimental diabetes rats, Tohoku J. Exp. Med., 129, 2, 139–49, 1979). These confirmed that peripheral nerve fibers of model rats for diabetic neuropathy were morphologically impaired and NCV was reduced. In addition to that, they reported that when insulin was administered to the rats, improvements in NCV could been observed, thus finding that control over blood glucose level led to improvements in NCV.

Since then, tests measuring NCV have been always conducted to evaluate the therapeutic efficacy of diabetic neuropathy. Afterward, no adequate results, however, have been practically provided by the treatments for diabetic neuropathy targeting improvements of NCV. In detail, Pietri A, et al. (Changes in nerve conduction velocity after six weeks of glucoregulation with portable insulin infusion pumps.: Diabetes, 29, 8, 668, 1980) and Graf R J, et al. (Glycemic control and nerve conduction abnormalities in non-insulin-dependent diabetic subjects: Ann. Intern. Med., 94, 3, 307, 1981) separately gave drug therapies using insulin to patients with insulin-dependent diabetes and patients with non-insulin-dependent diabetes in 1980 and 1981, respectively, in order to treat diabetic neuropathy. It was consequently reported that motor nerve conduction velocity (MCV) was improved by controlling blood glucose level. It was also reported, however, that only by controlling blood glucose level, improvements in sensory nerve conduction velocity (SCV) could not be observed, and that treatments mainly proposing to control blood glucose level, accordingly, only provided very limited improvements of functions such as thermal sensitivity and vibratory sensibility.

Although Pfeifer M A (Effects of glycemic control and aldose reductase inhibition on nerve conduction velocity: Am. J. Med., 79, 5A, 18–23, 1985) and Yoshio Goto, et al. (Clinical research for diabetic neuropathy using epalrestat (ONO-2235)—Inter-group double-blind placebo (including a trace amount of a curative medicine)-controlled trial: Igaku-no-Ayumi, 152, 6, 405, 1990) tested treatments using aldose reductase inhibitors (ARIs) based upon a hypothesis of abnormality in polyol metabolic pathway as one of the candidates of the cause of the disease in 1985 and 1990, respectively, the effects of aldose reductase inhibitors (ARIs) on improving motor nerve conduction velocity (MCV) and sensory nerve conduction velocity (SCV) remained low.

Accordingly, current methods of treatment for diabetic neuropathy, dietary therapy and administration of insulin, both mainly proposing to control blood glucose level, administration of aldose reductase inhibitors and aminoguanidine, both mainly proposing to improve abnormal glucose metabolism, administration of troglitazone, and administration of agents for limb ischemia mainly proposing to improve blood flow, have been conducted.

In any treatments, improvement of nerve conduction velocity was not always sufficient when a single drug was used, and methods of treatment by combined use of different therapeutic agents which have different functions have yet to be established. Accordingly, combined drug therapies for diabetic neuropathy, aiming at recovering once reduced nerve conduction velocity, have not yet been confirmed.

It has been reported that therapeutic efficacy obtained by single use of an anti-diabetic agent has achieved only limited improvements, i.e., applying 12-week treatment using an aldose reductase inhibitor alone (for 86 subjects), MCV (median motor nerve conduction velocity) and SCV (median sensory nerve conduction velocity) achieved improvement by only 2 m/sec and 3.2 m/sec, respectively. (Clinical research on diabetic neuropathy using epalrestat (ONO-2235)—Double-blind placebo (including a trace amount of a curative medicine)-controlled trial): Igaku-no-Ayumi, 152, 6, 405, 1990). In addition, when treatments with single use of an oral hypoglycemic agent (for 51 subjects) or an insulin (for 10 subjects) had been continued separately for 5 through 10 years, both nerve conduction velocities were rather reduced, i.e. MCV (median motor nerve conduction velocity) and SCV (median sensory nerve conduction velocity) were reduced by 2.9 m/sec and 0.6 m/sec, respectively (Juhani Partanen et al., Natural history of peripheral neuropathy in patients with non-insulin-dependent diabetes mellitus: N. Eng. J. Med., 333, 2, 89–94, 1995). Accordingly, it has been found that using methods of treatment with an anti-diabetic agent alone, nerve conduction velocities were only improved 3.2 m/sec at the best. Even in some cases these velocities rather were reduced as the illness proceeded.

It has been verified through animal experiments using beraprost, a prostaglandin-12 derivative, that beraprost has therapeutic efficacy on diabetic neuropathy. (Publication of unexamined application for Japanese Patent: Serial Number 1990-262519). No reports, however, have been published on combined effects of beraprost with an anti-diabetic agent on diabetic neuropathy aiming at functional improvements of sensory nerve and motor nerve.

As described hereinbefore, in the treatments of diabetic neuropathy aiming at recovering once-reduced nerve conduction velocity, any of the conventional anti-diabetic agents with its single use even shows some effects, but the degrees of which are not evaluated as clinical satisfaction. Moreover, no combined therapies using two curative agents with different functions have yet been achieved.

SUMMARY OF THE INVENTION

The present invention relates to a method of treatment of diabetic neuropathy characterized by combined administration of a prostaglandin-I$_2$ derivative, especially a formulation whose active ingredient is a prostaglandin-I$_2$ derivative with an anti-diabetic agent. The present invention specifically provides a method of treatment to deliver functional recoveries by targeting improvements in motor and sensory nerve conduction velocities for hypofunction of a motor nerve and sensory nerve to which conventional anti-diabetic drugs could not provide adequate treatment.

DESCRIPTION OF THE PREFERRED EMBODIMENT

Figure 1:
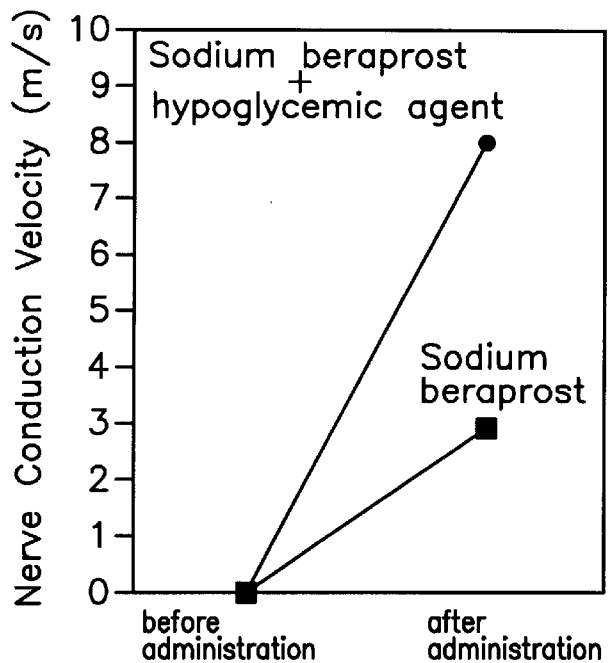
FIG. 1 represents therapeutic efficacy of combined use of sodium beraprost with an oral hypoglycemic agent on median nerve conduction velocity.

In accordance with this invention, the following may be employed: prostaglandin I, derivatives, prostaglandin I$_2$ derivatives, prostaglandin I$_3$, derivatives or salts thereof, and preferably prostaglandin I$_2$ derivatives or salts thereof are used. More preferably, derivatives of 4, 8-inter-m-phenylene prostaglandin I$_2$ are used. They are represented by the following general formula (I)

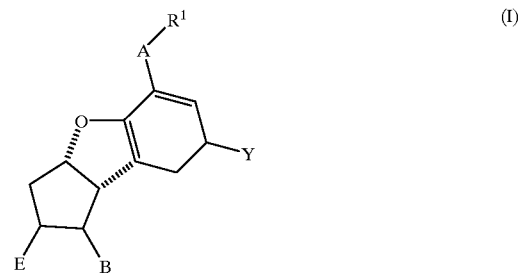

(I)

wherein R$^1$ represents
  (A) COOR$^2$ wherein R$^2$ represents
    1) hydrogen or pharmacologically acceptable positive ion, or
    2) straight alkyl containing 1–12 carbons or branched alkyl containing 3–14 carbons, or
    3) —Z—R$^3$
      wherein Z represents a valence bond, or a straight or branched alkylene group represented by C$_t$H$_{2t}$, wherein t represents an integer from 1–6, and wherein R$^3$ represents cycloalkyl containing 3–12 carbons or substituted cycloalkyl containing 3–12 carbons substituted with 1–3 groups of R$^4$, wherein R$^4$ represents hydrogen or alkyl containing 1–5 carbons,
    4) —(CH$_2$CH$_2$O)$_n$CH$_3$
      wherein n represents an integer of 1–5,
    5) —Z—Ar$^1$
      wherein Z has the same meaning as defined above, and Ar$^1$ is selected from the group consisting of phenyl, α-naphthyl, β-naphthyl, 2-pyridyl, 3-pyridyl, 4-pyridyl, α-furyl, β-furyl, α-thienyl, β-thienyl, or substituted phenyl (wherein the substituted phenyl is substituted by at least one substitute of chlorine, bromine, fluorine, iodine, trifluoromethyl, alkyl containing 1–4 carbons, nitro, cyano, methoxy, phenyl, phenoxy, p-acetamidobenzamide, —CH=N—NH—C(=O)—NH$_2$, —NH—C(=O)—Ph, —NH—C(=O)—CH$_3$ or —NH—C(=O)—NH$_2$).
    6) —C$_t$H$_{2t}$COOR$^4$
      wherein C$_t$H$_{2t}$ and R$^4$ have the same meanings as defined above,
    7) —C$_t$H$_{2t}$N(R$^4$)$_2$
      wherein C$_t$H$_{2t}$ and R$^4$ have the same meanings as defined above,
    8) —CH(R$^5$)—C(=O)—R$^6$
      wherein R$^5$ represents hydrogen or benzoyl, and R$^6$ represents phenyl, p-bromophenyl, p-chlorophenyl, p-biphenyl, p-nitrophenyl, p-benzamidophenyl or 2-naphthyl, 9) —$C_pH_{2p}$—W—$R^7$
   wherein W represents —CH=CH—, —CH=$CR^7$— or —C≡C—, and wherein $R^7$ represents hydrogen or straight or branched alkyl or aralkyl groups containing 1–30 carbons, and p represents an integer of 1–5, or 10) —CH($CH_2OR^3$)$_2$
    wherein $R^3$ represents alkyl or acyl containing 1–30 carbons, (B) —$CH_2OH$ (C) —C(=O)N($R^9$)$_2$
   wherein $R^9$ represents hydrogen or straight alkyl containing 1–12 carbons, branched alkyl containing 3–12 carbons, cycloalkyl containing 3–12 carbons, cycloalkylalkylene containing 4–13 carbons, phenyl, substituted phenyl (wherein the substitutes are the same as defined for (A) 5 described above), aralkyl containing 7–12 carbons, or —$SO_2R^{10}$, where $R^{10}$ represents alkyl containing 1–10 carbons, cycloalkyl containing 3–12 carbons, phenyl, substituted phenyl, wherein the substitutes are the same radical as defined for (A) 5 described above), aralkyl containing 7–12 carbons, provided that the two $R^9$s are the same or different, but when one represents —$SO_2R^{10}$, the other does not represent —$SO_2R^{10}$, or (D) —$CH_2OTHP$ (THP represents tetrahydropyranyl), where A represents
   1) —(CH$_2$)$_m$—
   2) —CH=CH—CH$_2$—
   3) —CH$_2$—CH=CH—
   4) —CH$_2$—O—CH$_2$—
   5) —CH=CH—
   6) —O—CH$_2$— or
   7) —C≡C—,
      wherein m represents an integer of 1–3, Y represents hydrogen, alkyl containing 1–4 carbons, chlorine, bromine, fluorine, formyl, methoxy or nitro, and where B represents
      —X—C($R^{11}$)($R^{12}$)O$R^{13}$
      wherein $R^{11}$ represents hydrogen or alkyl containing 1–4 carbons, $R^{13}$ represents hydrogen or acyl containing 1–14 carbons, aroyl containing 6–15 carbons, tetrahydropyranyl, tetrahydrofuranyl, 1-ethoxyethyl or t-butyl, X represents
      1) —CH$_2$—CH$_2$—
      2) —CH=CH— or
      3) —C≡C—, and $R^{12}$ represents
1) straight alkyl containing 1–12 carbons, branched alkyl containing 3–14 carbons, or
2) —Z—Ar$^2$
   wherein Z has the same meaning as defined above, Ar$^2$ represents phenyl, α-naphthyl, β-naphthyl, or at least one chlorine, bromine, fluorine, iodine, trifluoromethyl, alkyl containing 1–4 carbons, nitro, cyano, methoxy, phenyl or phenoxy-substituted phenyl, or
3) —$C_tH_{2t}$O$R^{14}$
   wherein $C_tH_{2t}$ has the same meaning as defined above, $R^{14}$ represents straight alkyl containing 1–6 carbons, branched alkyl containing 3–6 carbons, phenyl, or at least one chlorine, bromine, fluorine, iodine, trifluoromethyl, alkyl containing 1–4 carbons, nitro, cyano, methoxy, phenyl or phenoxy-substituted phenyl, cyclopenthyl, cyclohexyl, or substituted cyclopenthyl or cyclohexyl with 1–4 straight alkyls containing 1–4 carbons, or
4) —Z—$R^3$
   wherein Z and $R^3$ have the same meanings as defined above, or
5) —$C_tH_{2t}$—CH=C($R^{15}$)$R^{16}$
   wherein $C_tH_{2t}$ has the same meaning as defined above, $R^{15}$ and $R^{16}$ independently represent hydrogen, or methyl, ethyl, propyl or butyl, or
6) —$C_uH_{2u}$—C≡C—$R^{17}$
   wherein u represents an integer of 1–7, —$C_uH_{2u}$— represents straight or branched alkylene, and $R^{17}$ represents straight alkyl containing 1–6 carbons, and E represents hydrogen or —O$R^{18}$
   wherein $R^{18}$ represents acyl containing 1–12 carbons, aroyl consisting of 7–15 carbons, or $R^2$ (wherein $R^2$ has the same meaning as defined above), and the general formula can be in the isomeric d-form, l-form or dl-form, or pharmacologically acceptable salts thereof.

Specific examples of preferred prostaglandin I derivatives of the present invention, but not limited thereto, include beraprost identified as (II) below:

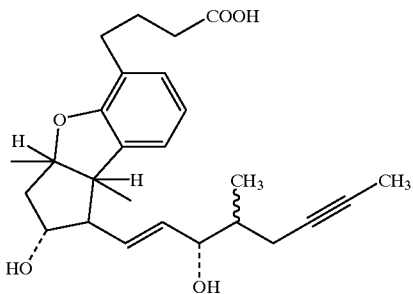

(II)

or salts thereof, ataprost, iloprost, clinprost, ciprostene, naxaprostene, taprostene, cicaprost, pimilprost, CH-169 and CS570.

Although the prostaglandin I derivatives of the present invention can be produced by well-known methods, the compounds shown in the general formula (I) or salts thereof, for example, can be produced in accordance with the method described in Publication of examined application for Japanese Patent, Serial Number 1989-53672.

The prostaglandin I derivatives of the present invention are generally used as, but not limited to, general formulations for oral administration use, such as tablets, capsules, powders, granules, or liquids combined with medically acceptable carriers or vehicles.

As anti-diabetic agents used in the present invention, but not limited thereto as long as they serve as medicines for diabetes, insulin and oral anti-diabetic agents, for example, can be used. Oral hypoglycemic agents, which are oral anti-diabetic agents, can be categorized into the following four groups, those embraced in any of which can be utilized in the present invention. The representative formulations in each group are follows.

(1) sulfonylureas:
   tolbutamide formulations, chlorpramide formulation, tolazamide formulations, acetohexamide formulations, glibenclamide formulations and gliclazide formulations, (2) bigdanides:
   buformin hydrochloride formulations, metformin formulations, (3) α-glycosidase inhibitors:
   acarbose formulations, voglibose formulations,
(4) agents for insulin-resistance:
   noscal.

One or more of the above-mentioned anti-diabetic agents can be administered in combined therapy.

Use and dose of the prostaglandin I derivatives and anti-diabetic agents are, but not limited to, those for single use of each medicine, in principle. A medicine which includes a prostaglandin I derivative as an active ingredient is administered in a daily dose of 0.01–100 mg per patient in 1–3 portions.

Although one or more of the prostaglandin I derivatives may be used as it is or as they are, it/they can be orally administered in the form of a solid including additive agents as shown hereinafter.

As the additive agents, vehicles such as starches, lactose, sucrose, glucose, mannitol, calcium carbonate, calcium sulfate and others: binders such as starches, dextrin, gum Arabic, gum tragacanth, methylcellulose, gelatin, polyvinylpyrrolidone, polyvinylalcohol, and others; disintegrators such as starches, polyvinylpyrrolidone, crystalline cellulose and the others; lubricants such as magnesium stearate, talc and the others; and coloring agents and flavors are useful.

The prostaglandin I derivatives of the present invention can be used in various dosage forms, but specifically the conventional dosage forms such as tablets, sugar-coated tablets, powders, troches, capsules, balls, syrups and the others can be mentioned.

The prostaglandin I derivatives of the present invention can also be parenterally administered in the form of sterile liquid. Sodium chloride, glucose or the others can be added to the liquid in adequate amounts to make the sterile liquid isotonic.

In addition to the above-mentioned oral formulations, because a wide range of parenteral administration routes can be applied to the prostaglandin I derivatives of the present invention, the derivatives may be formulated into dosage forms for parenteral use such as various injections, suppositories and the like.

For combined administration of the prostaglandin I derivatives of the present invention with anti-diabetic agents, these two types of medicines do not always need to be simultaneously administered. Even time intervals within the degree, where the combined effects cannot be lost, may be placed between the times of administration of the two types of medicines.

The method of treatment for diabetic neuropathy of the present invention affords recoveries of once reduced nerve conduction velocities for unmyelinated fibers (C-fibers), small (thinly) myelinated fibers (Aγ-fibers, Aδ-fibers and B-fibers), large (thickly) myelinated fibers (Aα-fibers and Aβ-fibers), as well as reduced motor nerve functions and sensory nerve functions including cold, warm and vibratory sensibilities by improving blood flow of peripheral nerve fascicle.

EXAMPLES

The examples described hereinafter are to illustrate the present invention.

Example 1

Therapeutic efficacy of combined use of sodium beraprost with an oral hypoglycemic agent on median nerve conduction velocity.

To patients with diabetic neuropathy, sodium beraprost was administered alone for single use or with a gliclazide as an oral hypoglycemic agent for combined use, and then the degrees of improvement in medial nerve conduction velocity were compared. Specifically, one patient with diabetic neuropathy was allocated to each administration schedule for 24 weeks, i.e. a sodium beraprost administration schedule (40 μg t.i.d., the total dose of 120 μg per day) or a combined administration schedule of sodium beraprost (40 μg t.i.d., the total dose of 120 μg per day) with a gliclazide as an oral hypoglycemic agent (a single daily dose of 20 mg), and then median nerve conduction velocities before and after the administration were compared for each patient. Nerve conduction velocities were measured using electromyograph and then chances in observed velocities and rates of change over the velocities before the administration were used to evaluate the degrees of improvement of nerve functions. In the case of motor nerve conduction velocity, if ten percent of the initial measured value is recovered, it is generally considered that useful therapeutic efficacy is provided. As the result, the median nerve conduction velocities of the patient given sodium beraprost alone were 50.6 and 53.5 m/sec, respectively, before and after the administration, indicating that a slight improvement of 2.9 m/sec was brought about by the sodium beraprost administration. The rate of change over the value prior to administration was 5.7 percent of improvement. While the median nerve conduction velocities of the patients given the combined administration of sodium beraprost with the gliclazide were 42.6 and 50.6 m/sec, respectively, before and after administration, indicating that a 8.0 m/sec of improvement was brought about. The rate of change over the value before the administration was 18.8 percent, indicating that a significantly larger improving effect was obtained compared with that for the treatment with the single administration of sodium beraprost (FIG. 1). Accordingly, this result shows that the large therapeutic efficacy on median nerve conduction velocity was only achieved when the combined administration of sodium beraprost with the anti-diabetic agent was employed.

Example 2

Therapeutic efficacy of combined use of sodium beraprost and an oral hypoglycemic agent on tibial nerve conduction velocity.

In accordance with a similar method to that of Example 1, one patient with diabetic neuropathy was allocated to each administration schedule for 24 weeks, i.e. a sodium beraprost administration schedule or a combined administration schedule of sodium beraprost with a gliclazide as an oral hypoglycemic agent, and then tibial nerve conduction velocities before and after administration were compared for each patient. Nerve conduction velocities were measured using an electromyograph and then changes, of observed velocities and rates of change over the velocities before administration, were used to evaluate the degrees of improvement on nerve functions.

Figure 2:
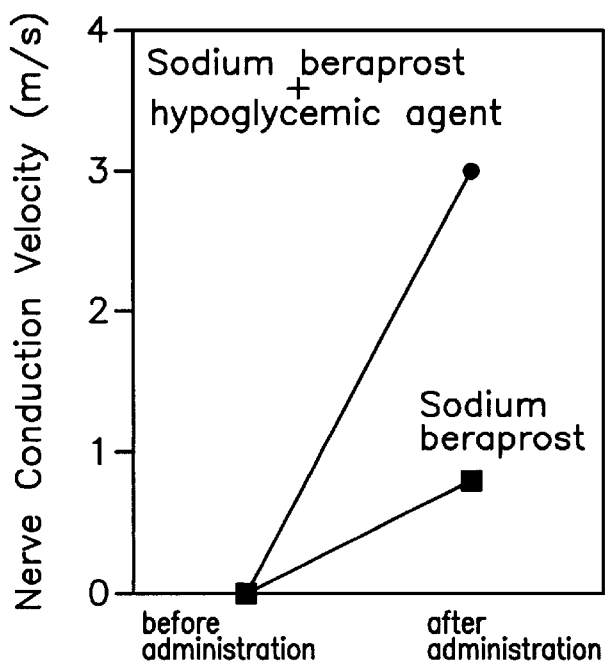
FIG. 2 represents therapeutic efficacy of combined use of sodium beraprost with an oral hypoglycemic agent on tibial nerve conduction velocity.

As a result, the tibial nerve conduction velocities of the patient given sodium beraprost alone were 38.5 and 39.3 m/sec, respectively, before and after the administration, indicating that a slight improvement of 0.8 m/sec by the sodium beraprost administration was brought about. The rate of change over the value before administration was 2.1 percent of improvement. The median nerve conduction velocities measured for the patients given the treatment of combined administration of sodium beraprost with gliclazide were 38.3 and 41.3 m/sec, respectively, before and after administration, indicating that a 3.0 m/sec of improvement was brought about. The rate of change over the value before administration was 7.8 percent, indicating that a remarkably larger improvement was obtained compared with that for treatment with administration of sodium beraprost alone (FIG. 2). Accordingly this result shows that a large therapeutic efficacy on tibial nerve conduction velocity was only achieved when the combined administration of sodium beraprost with the anti-diabetic agent was employed.

What is claimed is:

1. A method of treatment of diabetic neuropathy characterized by combined administration of a prostaglandin I derivative, as an active ingredient, with an anti-diabetic agent.

2. A method of improvement of sensory and/or motor nerve functions of a patient having diabetic neuropathy, comprising the combined administration to said patient of a prostaglandin I derivative, as an active ingredient, with an anti-diabetic agent.

3. The method according to claim 1 or 2, wherein said prostaglandin I derivative is a prostaglandin $I_2$ derivative or a pharmacologically acceptable salt thereof.

4. The method according to claim 1 or 2, wherein said prostaglandin I derivative is 4, 8-inter-m-phenylene prostaglandin $I_2$ represented by the following general formula (I):

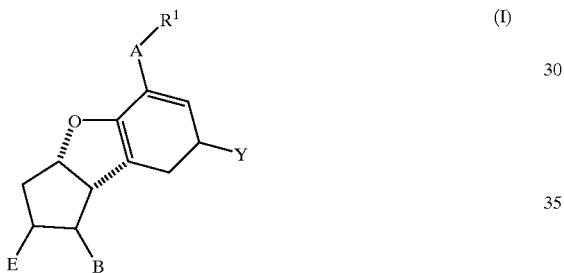

wherein $R_1$ represents
(A) $COOR^2$ wherein $R^2$ represents
1) hydrogen or pharmacologically acceptable positive ion, or
2) straight alkyl containing 1–12 carbons or branched alkyl containing 3–14 carbons, or
3) —Z—$R^3$
wherein Z represents a valence bond, or a straight or branched alkylene group represented by $C_tH_{2t}$ wherein t represents an integer from 1–6, and wherein $R^3$ represents cycloalkyl containing 3–12 carbons or substituted cycloalkyl containing 3–12 carbons substituted with 1–3 groups of $R^4$, wherein $R^4$ represents hydrogen or alkyl containing 1–5 carbons,
4) —(CH$_2$CH$_2$O)$_n$CH$_3$
wherein n represents an integer of 1–5,
5) —Z—Ar$^1$
wherein Z has the same meaning as defined above, and Ar$^1$ is selected from the group consisting of phenyl, α-naphthyl, β-naphthyl, 2-pyridyl, 3-pyridyl, 4-pyridyl, α-furyl, β-furyl, α-thienyl, β-thienyl, or substituted phenyl (wherein the substituted phenyl is substituted by at least one substitute of chlorine, bromine, fluorine, iodine, trifluoromethyl, alkyl containing 1–4 carbons, nitro, cyano, methoxy, phenyl, phenoxy, p-acetamidobenzamide, —CH=N—NH—C(=O)—NH$_2$, —NH—C(=O)—Ph, —NH—C(=O)—CH$_3$ or —NH—C(=O)—NH$_2$)
6) —C$_t$H$_{2t}$COOR$^4$
wherein C$_t$H$_{2t}$ and $R^4$ have the same meanings as defined above,
7) —C$_t$H$_{2t}$N(R$^4$)$_2$
wherein C$_t$H$_{2t}$ and $R^4$ have the same meanings as defined above,
8) —CH(R$^5$)—C(=O)—R$^6$
wherein $R^5$ represents hydrogen or benzoyl, and $R^6$ represents phenyl, p-bromophenyl, p-chlorophenyl, p-biphenyl, p-nitrophenyl, p-benzamidophenyl or 2-naphthyl,
9) —C$_p$H$_{2p}$—W—R$^7$
wherein W represents —CH=CH—, —CH=CR$^7$— or —C≡C—, and wherein $R^7$ represents hydrogen or straight or branched alkyl or aralkyl groups containing 1–30 carbons, and p represents an integer of 1–5, or
10) —CH(CH$_2$OR$^3$)$_2$
wherein $R^3$ represents alkyl or acyl containing 1–30 carbons,
(B) —CH$_2$OH
(C) —C(=O)N(R$^9$)$_2$
wherein $R^9$ represents hydrogen or straight alkyl containing 1–12 carbons, branched alkyl containing 3–12 carbons, cycloalkyl containing 3–12 carbons, cycloalkylalkylene containing 4–13 carbons, phenyl, substituted phenyl (wherein the substitutes are the same as defined for (A) 5 described above), aralkyl containing 7–12 carbons, or —SO$_2$R$^{10}$, where $R^{10}$ represents alkyl containing 1–10 carbons, cycloalkyl containing 3–12 carbons, phenyl, substituted phenyl, wherein the substitutes are the same radical as defined for (A) 5 described above), aralkyl containing 7–12 carbons, provided that the two $R^9$s are the same or different, but when one represents —SO$_2$R$^{10}$, the other does not represent —SO$_2$R$^{10}$, or
(D) —CH$_2$OTHP (THP represents tetrahydropyranyl), where A represents
1) —(CH$_2$)$_m$—
2) —CH=CH—CH$_2$—
3) —CH$_2$—CH=CH—
4) —CH$_2$—O—CH$_2$—
5) —CH=CH—
6) —O—CH$_2$— or
7) —C≡C—,
wherein m represents an integer of 1–3, Y represents hydrogen, alkyl containing 1–4 carbons, chlorine, bromine, fluorine, formyl, methoxy or nitro, and where B represents
—X—C(R$^{11}$)(R$^{12}$)OR$^{13}$
wherein $R^{11}$ represents hydrogen or alkyl containing 1–4 carbons, $R^{13}$ represents hydrogen or acyl containing 1–14 carbons, aroyl containing 6–15 carbons, tetrahydropyranyl, tetrahydrofuranyl, 1-ethoxyethyl or t-butyl, X represents
1) —CH$_2$—CH$_2$—
2) —CH=CH— or
3) —C≡C—, and
$R^{12}$ represents
1) straight alkyl containing 1–12 carbons, branched alkyl containing 3–14 carbons, or
2) —Z—Ar$^2$ wherein Z has the same meaning as defined above, $Ar^2$ represents phenyl, α-naphthyl, β-naphthyl, or at least one chlorine, bromine, fluorine, iodine, trifluoromethyl, alkyl containing 1–4 carbons, nitro, cyano, methoxy, phenyl or phenoxy-substituted phenyl, or 3) —$C_tH_{2t}OR^{14}$ wherein $C_tH_{2t}$ has the same meaning as defined above, $R^{14}$ represents straight alkyl containing 1–6 carbons, branched alkyl containing 3–6 carbons, phenyl, or at least one chlorine, bromine, fluorine, iodine, trifluoromethyl, alkyl containing 1–4 carbons, nitro, cyano, methoxy, phenyl or phenoxy-substituted phenyl, cyclopenthyl, cyclohexyl, or substituted cyclopentyl or cyclohexyl with 1–4 straight alkyls containing 1–4 carbons, or

4) —Z—$R^3$ wherein Z and $R^3$ have the same meanings as defined above, or

5) —$C_tH_{2t}$—CH=C($R^{15}$)$R^{16}$ wherein $C_tH_{2t}$ has the same meaning as defined above, $R^{15}$ and $R^{16}$ independently represent hydrogen, or methyl, ethyl, propyl or butyl, or 6) —$C_uH_{2u}$—C≡C—$R^{17}$ wherein u represents an integer of 1–7, —$C_uH_{2u}$— represents straight or branched alkylene, and $R^{17}$ represents straight alkyl containing 1–6 carbons, and E represents hydrogen or —$OR^{18}$ wherein $R^{18}$ represents acyl containing 1–12 carbons, aroyl consisting of 7–15 carbons, or $R^2$ (wherein $R^2$ has the same meaning as defined above), and the general formula can be in the isomeric d-form, l-form or dl-form, or pharmacologically acceptable salts thereof.

5. The method according to claim 1 or 2, wherein said prostaglandin I derivative is beraprost or a salt thereof.

6. The method according to claim 1 or 2, wherein said prostaglandin I derivative is selected from the group consisting of ataprost, iloprost, clinprost, ciprostene, naxaprostene, taprostene, cicaprost, pimilprost, CH-169 and CS570.

7. The method according to claim 1 or 2, wherein said anti-diabetic drug is an insulin formulation.

8. A method as defined in claim 1 or 2, wherein said prostaglandin I derivative is beraprost or a salt thereof and said anti-diabetic agent is an insulin formulation.

9. The method according to claim 1 or 2, wherein said anti-diabetic drug is an oral anti-diabetic agent.

10. The method according to claim 1 or 2, wherein said prostaglandin I derivative in beraprost or a salt thereof and said anti-diabetic agent is an oral anti-diabetic agent.

* * * * *